United States Patent [19]

Dubroeucq et al.

[11] Patent Number: 4,499,094
[45] Date of Patent: Feb. 12, 1985

[54] DERIVATIVES OF ARENE AND HETERO-ARENE CARBOXAMIDES AND THEIR USE AS MEDICAMENTS

[75] Inventors: Marie-Christine Dubroeucq, Enghien-les-Bains; Christian Renault, Taverny; Gérard Le Fur, Plessis Robinson, all of France

[73] Assignee: Pharmuka Laboratoires, Gennevilliers, France

[21] Appl. No.: 482,082

[22] Filed: Apr. 5, 1983

[30] Foreign Application Priority Data

Apr. 27, 1982 [FR] France ................... 82 07217

[51] Int. Cl.³ .................. A61K 31/435; C07D 495/04
[52] U.S. Cl. .................................... 514/301; 549/77;
564/162; 514/259; 564/166; 564/172; 514/311;
514/314; 514/307; 514/351; 514/357; 514/438;
514/613; 544/116; 544/119; 544/127; 544/128;
544/131; 544/158; 544/162; 544/174; 544/176;
544/283; 544/284; 544/360; 544/362; 544/379;
544/391; 546/114; 546/144; 546/167; 546/169;
546/194; 546/281; 546/334; 548/527; 548/539
[58] Field of Search ............... 546/114, 144, 167, 169,
546/194, 281, 334; 544/116, 119, 128, 127, 131,
158, 162, 174, 283, 284, 360, 362, 379, 391, 176;
548/539, 527; 549/77; 564/162, 166, 172;
424/248.56, 251, 256, 250, 263, 275, 320

[56] References Cited

U.S. PATENT DOCUMENTS 1,069,296  8/1913  Schwabe ............... 546/169
4,402,961  9/1983  Dubroeucq et al. ............ 546/167

FOREIGN PATENT DOCUMENTS 764299  8/1971  Belgium .
  3920  9/1979  European Pat. Off. .

OTHER PUBLICATIONS

Fryer et al., J. of Org. Chem., vol. 32, No. 12, Dec. 1967, pp. 3798–3803.

Primary Examiner—Henry R. Jiles
Assistant Examiner—Bernard I. Dentz
Attorney, Agent, or Firm—Beveridge, DeGrandi & Kline

[57] ABSTRACT

Compounds with the formula:

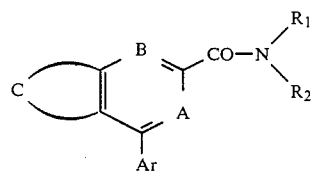

in which $R_1$ and $R_2$ represent independently, a linear or branched alkyl, cycloalkyl, phenylalkyl or cycloalkylalkyl group. $R_1$ and $R_2$ may also represent an alkenyl or alkynyl group. $R_1$ and $R_2$ may also represent a group of the formula $-R_3-Z-R_4$ in which $R_3$ represents an alkylene group, on condition that at least 2 carbon atoms separate the nitrogen atom from the group Z; $R_4$ represents an alkyl group, and Z an atom of oxygen, sulphur or the group $>N-R_5$, $R_5$ representing a hydrogen atom or an alkyl group. $R_1$ and $R_2$ may form, with the nitrogen atom to which they are attached, a heterocyclic ring. Ar represents a phenyl, pyridyl or thienyl group, or a substituted phenyl group, A and B representing independently, N or CH—, the group C representing the residue of a benzene or thiophene ring. These compounds can be used as medicaments, in particular, for the various applications of benzodiazepines.

11 Claims, No Drawings

DERIVATIVES OF ARENE AND HETERO-ARENE CARBOXAMIDES AND THEIR USE AS MEDICAMENTS

The various clinical effects (anxiolytic, anticonvulsant, hypnotic, myorelaxant) of benzodiazepines, have been attributed to the presence within the central nervous system of mammals, of saturable binding sites with a high affinity and stereospecificity. (C. BRAESTRUP et al., Nature 1977, 269, 702; J. F. TALLMANN et al., Science, 1980, 207, 274).

Some benzodiazepines also bind to membranes of peripheral tissue, such as the kidney, also with a high affinity (C. BRAESTRUP et al., Proc. Natl. Acad. Sci. USA, 1977, 74, 3805). Benzodiazephine receptors present in these tissues differ from those marked by ($^3$H) diazepam or ($^3$H) flunitrazepam in the brain; for example, clonazepam, which has a very strong affinity for the binding sites of ($^3$H) diazepam in the brain, is practically inactive with regard to the binding sites of ($^3$H) diazepam in the kidney. On the contrary, a chlorinated derivative of diazepam, Ro-5-4864, is very active at the peripheral level, but inactive at the central level. Therefore, it is possible to distinguish at least 2 types of benzodiazepine receptors, one of the "cerebral" type, the pharmacological criteria for which is a classification by decreasing affinity in the following order: clonazepan > diazepam > Ro-5-4864, and the other of the "peripheral" type, the pharmacological criteria for which is a classification by decreasing affinity in the following order: Ro-5-4864 > diazepam > clonazepam.

These receptors, of the "peripheral" type, are present in many organs: the heart, the kidney, the lung, blood platelets and also the brain (where the two types of receptor are present) (L. P. DAVIES et al., Eur. J. Pharmacol., 1981, 73, 209; J. K. T. WANG et al, Life Sciences, 1980, 27, 1881; J. W. REGAN et al, Life Sciences, 1981, 28, 991; H. SCHOEMAKER, Eur. J. Pharmacol., 1981, 71, 173). At last it has been shown the presence of these receptors of the "peripheral" type in the thymocytes (J. K. T. WANG et al., Pharmacologist, 1981, 23, 160) and that these receptors regulate the proliferation of cells of thymones (J. K. T. WANG et al., Fed. Proc. 1982, 41, 1328).

The present invention is concerned with new compounds which, while having different structures from those of the benzodiazepines, specifically bind to benzodiazepine receptors of the "peripheral" type. These compounds may be represented by the general formula:

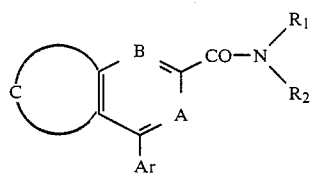

in which $R_1$ and $R_2$ independently represent a linear or branched alkyl group containing 1 to 6 carbon atoms, a cycloalkyl group containing 3 to 7 carbon atoms, a phenyl alkyl or cycloalkylalkyl group, the alkyl part of which contains from 1 to 3 carbon atoms. $R_1$ and $R_2$ can also represent an alkenyl or alkynyl group containing from 3 to 6 carbon atoms, on condition that the double or triple bond is not situated in position 1-2 with respect to the nitrogen atom. $R_1$ and $R_2$ may also represent a group of the formula $-R_3-Z-R_4$, in which $R_3$ represents a linear or branched alkylene group with 2 to 6 carbon atoms, on condition that at least 2 carbon atoms separate the nitrogen atom from the group Z; $R_4$ represents an alkyl group containing from 1 to 4 carbon atoms and Z represents an atom of oxygen, sulphur, or the group $>N-R_5$, where $R_5$ represents an atom of hydrogen or an alkyl group with 1 to 3 carbon atoms.

Furthermore, $R_1$ and $R_2$ may form, together with the nitrogen atom to which they are attached, a heterocyclic group which may include a second hetero-atom: nitrogen or oxygen; that is to say that:

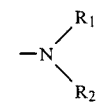

may represent a pyrrolidine, piperidine, morpholine or piperazine ring, which may be substituted at the nitrogen atom with an alkyl group having from 1 to 3 carbon atoms.

Ar represents a phenyl, pyridyl or thienyl group, or a phenyl group substituted with one or two substituents selected from halogen atoms (chlorine, fluorine, bromine), alkyl, alkoxy and alkylthio groups having 1 to 4 carbon atoms, the trifluoromethyl group and the nitro group.

The groups A and B represent independently, N or CH—.

The group C< represents the linkage

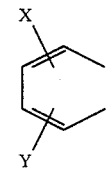

or, when A represents N and B represents CH, one of the following linkages:

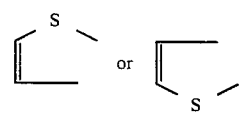

In other words, the products with formula I in the present invention, correspond to one of the 3 formulae below:

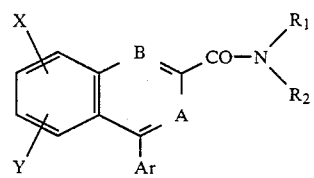

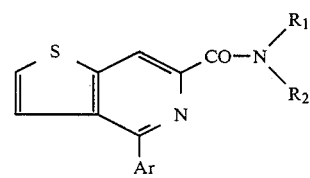

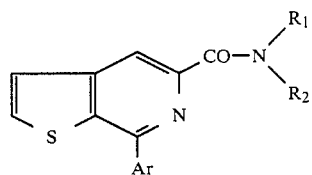

In the formulae II, III and IV, $R_1$, $R_2$, Ar, A and B have the meaning described above; X and Y represent independently, a hydrogen atom, a halogen atom (fluorine, chlorine, bromine), an alkyl or alkoxy group containing 1 to 3 carbon atoms, the nitro or trifluoromethyl group. A feature of the invention are compounds of formulae II, III and IV wherein:

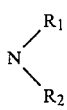

is a ring structure identified above.

When the group:

contains an asymmetric carbon atom, the products with formula I can be resolved into optical opposites. In this case, each enantiomer and the racemic compound are a part of the invention.

The products with general formula I may be prepared from acids with formula V and the amines:

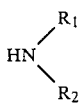

by known methods which allow the conversion of a carboxylic acid into a carboxamide, by way of a reactive derivative VI of the carboxylic acid, in accordance with the following scheme:

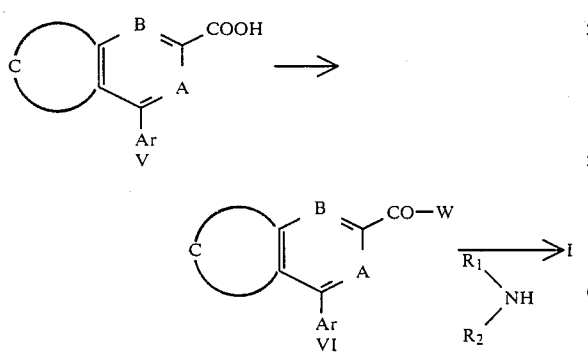

Reactive derivatives having the formula VI are generally esters (W represents an alkoxy group of low molecular weight), acid chlorides (W represents a chlorine atom) and anhydrides (W represents an alkoxycarbonyloxy group of low molecular weight), (cf. C. A. BUEHLER and D. E. PEARSON, Survey of Organic Synthesis, Wiley Interscience, 1970, page 894).

Esters of formula VI may be prepared by heating acids of formula V, in the presence of an alcohol of low molecular weight such as methanol or ethanol, under reflux and in the presence of a mineral acid such as sulphuric or hydrochloric acid. The esters thus obtained, are then treated with at least one equivalent of the amine:

in the presence of a metallizing agent such as butyl-lithium, in the presence of an inert solvent such as ethyl ether or tetrahydrofuran, at a temperature between $-10°$ and $+30°$ C.

Acid chlorides of formula VI can be prepared by the action of a chlorinating agent such as thionyl chloride on the corresponding acids with formula V, in the absence of solvent, or in the presence of an inert solvent such as chloroform, and under reflux. The crude acid chloride thus obtained, is then treated with the amine:

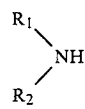

in the presence of inert solvent such as toluene or chloroform and at ambient temperature. It is advantageous to operate in the presence of an excess of at least one equivalent of amine, which acts as a base neutralizing the hydrochloric acid formed. It is also possible to operate in the presence of pyridine, which acts as a base and solvent at the same time.

Mixed anhydrides of formula VI, may be prepared by treating the corresponding acids of formula V, with an alkyl chloroformate Cl—COO—R' (R' representing an alkyl group of low molecular weight, such as methyl or ethyl) in the presence of a tertiary amine such as triethylamine; the product obtained is then treated with the amine:

It is advantageous to carry out the two reactions in the same apparatus, without isolating the mixed anhydride. This is prepared at a temperature between $-5$ and $+25°$ C., in the presence of an inert solvent such as chloroform or methylene chloride, and then the amine:

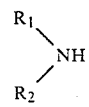

is added, either in the pure form, or in solution in an inert solvent such as benzene, toluene, chloroform or methylene chloride at the same temperature.

Carboxylic acids of the general formula V, belong, according to the significance of A, B and C, to one of the families defined by the formulae below:

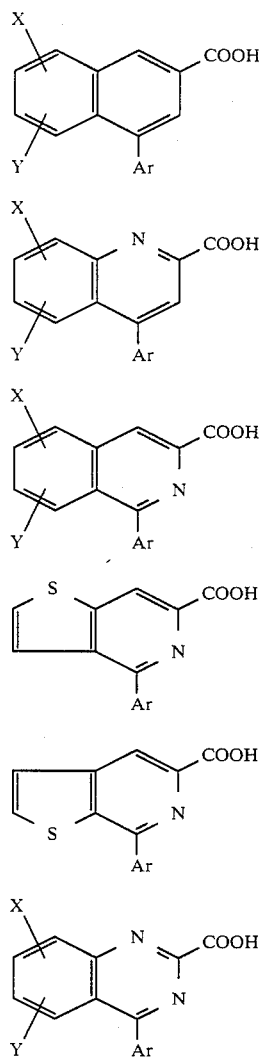

Some compounds of formula VII are known; in particular, 4-phenyl naphthalene 2-carboxylic acid. Compounds of formula VII may be prepared by applying to appropriate precursors, the reactions used for the preparation of known derivatives (R. FILLER et al., J. Org. Chem., 1962, 27, 4440).

In the same way, carboxylic acids with formula VIII may be prepared by analogy with the process described for the preparation of known products of formula VIII (K. TAKAHASHI et al., J., Heterocycl. Chem., 1977, 14, 881).

Among the compounds of formula IX, several are known, in particular 1-phenyl isoquinoline 3-carboxylic acid. (R. FILLER et al., J. Org. Chem., 1962, 27, 2403; D. A. WALSH et al., J. Med. Chem., 1978, 21, 582). The processes described in these publications may be used in analogous manner for the preparation of products of formula IX, starting from appropriate precursors.

The compounds of formulae X and XI are new and are therefore a feature of the invention. For their preparation, it is advantageous to use a process modified with regard to that described by R. FILLER et al (J. Org. Chem., 1962, 27, 2403) according to the following reaction scheme:

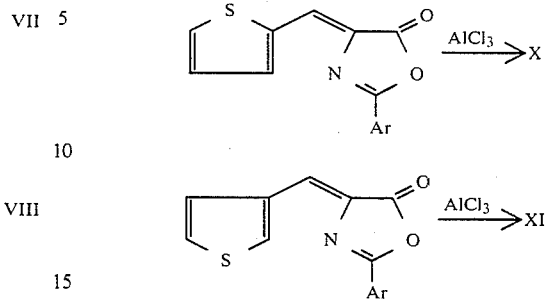

In order to carry out these reactions, the initial oxazolones of X or XI, are treated with 3 equivalents of aluminum chloride in the presence of 1,1,2,2-tetrachloroethane at a temperature between 20° C. and the boiling point of the solvent.

Several compounds of formula XII are known, (notably those products in which X represents a hydrogen atom, Y a chlorine atom in the 6 position, and Ar the phenyl or 2-chlorophenyl group), and these have been obtained starting from benzodiazepines (STERNBACH, et al., J. Org. Chem., 1964, 29, 332). Nevertheless, it is more advantageous to prepare these compounds and all compounds with formula XII, starting from 2-aroyl anilines with formula XIII, according to the following reaction scheme:

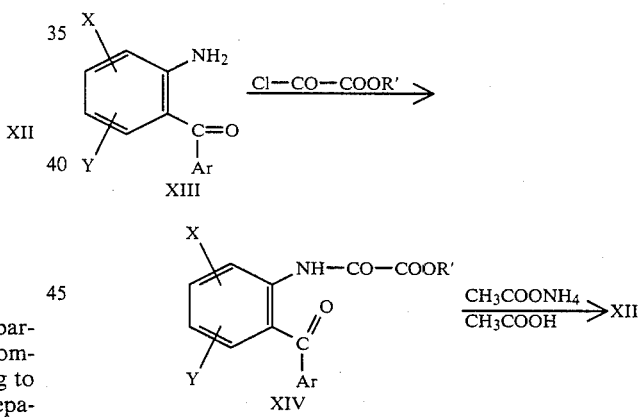

The 2-aroyl anilines of formula XIII, are treated with at least 1 equivalent of an alkoyloxalyl chloride Cl—CO—COOR' (R' represents an alkyl group of low molecular weight such as methyl or ethyl), in the presence of pyridine, at a temperature between 0° and 25° C. The compound of formula XIV thus prepared, is then treated with a large excess of ammonium acetate in the presence of acetic acid, under reflux.

The reaction mixtures obtained by the various processes described above, are treated according to classical methods, either physical (evaporation, solvent extraction, distillation, crystallization, chromatography, etc.) or chemical (formation of a salt and regeneration of the base or the acid, etc.) as appropriate, in order to isolate the compounds with formula I, in a pure state.

The following examples illustrate the invention, without limiting it.

EXAMPLE 1

N,N-diethyl 4-phenyl naphthalene 2-carboxamide 4 g of 4-phenyl naphthalene 2-carboxylic acid in 16 ml of thionyl chloride, are kept for 4 h. at 80° C., and then concentrated to dryness under reduced pressure. The residue is taken up again in 20 ml of pyridine, and then 3.8 ml of diethylamine are added. After stirring for 2 h. at ambient temperature, the reaction mixture is poured into 200 ml of water, and the insoluble material extracted with 3 portions of ether, each of 80 ml. The organic phase is washed 3 times with 50 ml of water each time, 3 times with 50 ml of 0.1N hydrochloric acid each time, and once with 80 ml of water. After drying over magnesium sulphate, the product is evaporated to dryness under reduced pressure. After recrystallization of the solid residue from ethyl ether, 2 g of N,N-diethyl 4-phenyl naphthalene 2-carboxamide, melting at 130° C., are obtained.

4-phenyl naphthalene 2-carboxylic acid can be obtained according to R. FILLER et al., J. Org. Chem., 1962, 27, 4440.

EXAMPLE 2

N-methyl N(1-methyl propyl) 4-phenyl naphthalene 2-carboxamide

Operations are carried out as for Example 1, starting from 4.3 g of 4-phenyl naphthalene 2-carboxylic acid, 20 ml of thionyl chloride and then 1.5 g of N-methyl 2-butanamine in 20 ml of pyridine. 3 g of N-methyl N(1-methyl propyl) 4-phenyl naphthalene 2-carboxamide, melting at 108° C., are obtained.

EXAMPLE 3

N,N-diethyl 4-phenyl quinoline 2-carboxamide

The process is carried out as for Example 1, starting from 2 g of 4-phenyl quinoline 2-carboxylic acid, 6 ml of thionyl chloride and 8.3 ml of diethylamine. After treatment, 2.3 g of N,N-diethyl 4-phenyl quinoline 2-carboxamide are isolated in the form of an orange oil. After crystallization from a 50/50 hexane-ether mixture, the product has a melting point lower than 50° C.

4-phenyl quinoline 2-carboxylic acid may be prepared according to TAKAHASHI and MITSUHASHI, J. Het, Chem., (15), p. 881 (1977).

EXAMPLE 4

N,N-dimethyl 1-phenyl isoquinoline 3-carboxamide

To 1.1 g of dimethylamine in 20 ml of anhydrous tetrahydrofuran, are added, at −10° C. and under nitrogen, 10.5 ml of a 1.6M solution of butyl lithium in hexane. After stirring for 45 min., 2.2 g of ethyl 1-phenyl isoquinoline 3-carboxylate are added and agitation continued for 4 h. at ambient temperature. 50 ml of water are added, and the insoluble material extracted 3 times, each with 100 ml of ethyl acetate. The organic phase is dried over magnesium sulphate and evaporated to dryness under reduced pressure. The residue is recrystallized from isopropyl ether to give 1.5 g of N,N-dimethyl 1-phenyl isoquinoline 3-carboxamide, melting at 157° C.

Ethyl 1-phenyl isoquinoline 3-carboxylate can be prepared by the action of ethanol on 1-phenyl isoquinoline 3-carboxylic acid in the presence of concentrated sulphuric acid. It has a melting point of 114°–116° C.

1-phenyl isoquinoline 3-carboxylic acid can be prepared according to R. FILLER et al., J. Org. Chem., 1962, 27, 2403.

EXAMPLE 5

N,N-diethyl 1-phenyl isoquinoline 3-carboxamide

Operations are carried out as for Example 4, starting with 3.9 g of 1-phenyl isoquinoline 3-ethyl carboxylate, 3.4 g of diethylamine and 19 ml of a 1.6M solution of butyl lithium in hexane. 1.75 g of N,N-diethyl 1-phenyl isoquinoline 3-carboxamide, which melts at 72° C., are obtained.

EXAMPLE 6

N,N-diethyl 1-(2-chloro-phenyl) isoquinoline 3-carboxamide

Operations are carried out as for Example 4, starting with 3.4 g of ethyl 1-(2-chloro-phenyl) isoquinoline 3-carboxylate, 2.4 g of diethylamine and 14 ml of a 1.6M solution of butyl lithium in hexane. After chromatography on silica gel with a cyclohexane-ethyl acetate (1:1) mixture as eluant, and recrystallization from isopropyl ether, 0.85 g of N,N-diethyl 1-(2-chloro-phenyl) isoquinoline 3-carboxamide melting at 112° C., is obtained.

Ethyl 1-(2-chloro-phenyl) isoquinoline 3-carboxylate may be prepared by the action of ethanol on 1-(2-chloro-phenyl) isoquinoline 3-carboxylic acid in the presence of concentrated sulphuric acid. It has a melting point of 126° C.

1-(2-chloro-phenyl) isoquinoline 3-carboxylic acid can be obtained by the action of aluminum chloride (0.165 mole) on 2-(2-chloro-phenyl) 4-phenyl methylene 5-4H-oxazolone (0.055 mole) in 250 ml of tetrachloroethane, at ambient temperature. It has a melting point of 195°–196° C.

EXAMPLE 7

1-[3-(1-phenyl isoquinolyl) carbonyl]piperidine

To 3.74 g of 1-phenyl isoquinoline 3-carboxylic acid in 150 ml of chloroform are added 1.73 g of triethylamine. This is cooled to 10° C. and 1.86 g of ethyl chloroformate are added. After stirring for 40 min. at ambient temperature, a solution of 1.63 g of piperidine in 10 ml of toluene are added, and stirring continued for 4 h. at ambient temperature. The reaction medium is evaporated under reduced pressure, the residue taken up in ethyl acetate, the organic phase washed with a saturated aqueous solution of sodium carbonate, dried over magnesium sulphate and evaporated to dryness under reduced pressure. The residue is chromatographed on silica gel with a cyclohexane-ethyl acetate (1:1) mixture as eluant, and the product recrystallized from isopropyl ether. 2.4 g of 1-[3-(1-phenyl isoquinolyl) carbonyl]piperidine, which melts at 179° C., is obtained.

EXAMPLE 8

4-[3-(1-phenyl isoquinolyl) carbonyl]morpholine

Operations are carried out as for Example 7, starting with 3.74 g of 1-phenyl isoquinoline 3-carboxylic acid, 1.73 g of triethylamine, 1.86 g of ethyl chloroformate and 1.67 g of morpholine in 150 ml of chloroform.

3 g of 4-[3-(1-phenyl isoquinolyl) carbonyl]morpholine melting at 178° C., are obtained.

EXAMPLE 9

4-methyl 1-[3-(1-phenyl isoquinolyl) carbonyl]piperazine

Operations are carried out as for Example 7, starting with 3.74 g of 1-phenyl isoquinoline 3-carboxylic acid, 1.73 g of triethylamine, 1.86 g of ethyl chloroformate and 1.92 g of N-methyl piperazine in 150 ml of chloroform. 1.7 g of 4-methyl 1-[3-(1-phenyl isoquinolyl) carbonyl]piperazine, melting at 127° C., are obtained.

EXAMPLE 10

N-methyl N(1-methyl propyl) 1-phenyl isoquinoline 3-carboxamide

Operations are carried out as for Example 7, starting with 2.96 g of 1-phenyl isoquinoline 3-carboxylic acid, 1.33 g of triethylamine, 1.49 g of ethyl chloroformate and 1.34 g of N-methyl 2-butanamine in 120 ml of chloroform. 2.4 g of N-methyl N(1-methyl propyl) 1-phenyl isoquinoline 3-carboxamide melting at 95°–96° C., are obtained.

EXAMPLE 11

N,N-diethyl 1-(3-chlorophenyl) isoquinoline 3-carboxamide

Operations are carried out as for Example 7, starting with 1.7 g of 1-(3-chlorophenyl) isoquinoline 3-carboxylic acid, 0.69 g of triethylamine, 0.74 g of ethyl chloroformate and 0.56 g of diethylamine in 60 ml of chloroform. 1.45 g of N,N-diethyl 1-(3-chlorophenyl) isoquinoline 3-carboxamide melting at 116° C., are obtained.

1-(3-chlorophenyl) isoquinoline 3-carboxylic acid can be prepared by the action of aluminum chloride (0.369 mole) on 2-(3-chlorophenyl) 4-phenyl methylene 4H 5-oxazolone (0.123 mole) in 500 ml of tetrachloroethane, at ambient temperature. It has a melting point of 236° C.

EXAMPLE 12

N,N-diethyl 1-(4-methylphenyl) isoquinoline 3-carboxamide

Operations are carried out as for Example 7, starting from 5 g of 1-(4-methylphenyl) isoquinoline 3-carboxylic acid, 2.18 g of triethylamine, 2.39 g of ethyl chloroformate and 1.83 g of diethylamine in 190 ml of chloroform. 3.25 g of N,N-diethyl 1-(4-methylphenyl) isoquinoline 3-carboxamide melting at 113° C., are obtained.

1-(4-methylphenyl) isoquinoline 3-carboxylic acid can be obtained by the action of aluminum chloride (0.138 mole) on 2-(4-methylphenyl) 4-phenyl methylene 4H 5-oxazolone (0.046 mole) in 200 ml of tetrachloroethane, at 60° C. It has a melting point of 204° C.

EXAMPLE 13

1-[[1-(2-chlorophenyl) 3-isoquinolyl]carbonyl]piperidine

Operations are carried out as for Example 7, starting with 1.42 g of 1-(2-chlorophenyl) isoquinoline 3-carboxylic acid, 0.58 g of triethylamine, 0.62 g of ethyl chloroformate and 0.55 g of piperidine in 50 ml of chloroform. 1.2 g of 1-[[1-(2-chlorophenyl) 3-isoquinolyl]carbonyl]piperidine, melting at 161° C. is obtained.

EXAMPLE 14

N,N-dipropyl 1-(2-chlorophenyl) isoquinoline 3-carboxamide

Operations are carried out as for Example 7, starting from 1.42 g of 1-(2-chlorophenyl) isoquinoline 3-carboxylic acid, 0.58 g of triethylamine, 0.62 g of ethyl chloroformate and 0.66 g of N-propyl propylamine in 50 ml of chloroform. 1.40 g of N,N-dipropyl 1-(2-chloro phenyl) isoquinoline 3-carboxamide, melting at 101° C., are obtained.

EXAMPLE 15

N,N-diethyl 1-(3-fluoro phenyl) isoquinoline 3-carboxamide

Operations are carried out as for Example 7, starting from 1.32 g of 1-(3-fluoro phenyl) isoquinoline 3-carboxylic acid, 0.57 g of triethylamine, 0.62 g of ethyl chloroformate, and 0.47 g of diethylamine in 50 ml of chloroform. 1.86 g of N,N-diethyl 1-(3-fluoro phenyl) isoquinoline 3-carboxamide, melting at 92° C., are obtained.

1-(3-fluoro phenyl) isoquinoline 3-carboxylic acid is obtained by the action of aluminum chloride (0.219 mole) on 2-(3-fluoro phenyl) 4-phenyl methylene 4H 5-oxazolone (0.073 mole) in 120 ml of tetrachloroethane, at ambient temperature. It has a melting point of 240° C.

EXAMPLE 16

N-methyl N-(1-methyl propyl) 1-(2-fluoro phenyl) isoquinoline 3-carboxamide

Operations are carried out as for Example 7, starting from 2.3 g of 1-(2-fluoro phenyl) isoquinoline 3-carboxylic acid, 1 g of triethylamine, 1.06 g of ethyl chloroformate and 0.96 g of N-methyl 2-butanamine in 85 ml of chloroform. 1.85 g of N-methyl N-(1-methyl propyl) 1-(2-fluoro phenyl) isoquinoline 3-carboxamide, melting at 85° C., is obtained.

1-(2-fluoro phenyl) isoquinoline 3-carboxylic acid is obtained by the action of aluminum chloride (0.3 mole) on 2-(2-fluoro phenyl) 4-phenyl methylene 4H 5-oxazolone (0.1 mole) in 220 ml of tetrachloroethane, at ambient temperature. It has a melting point of 238° C.

EXAMPLE 17

N-methyl N-phenylmethyl 1-(2-chloro phenyl) isoquinoline 3-carboxamide

Operations are carried out as for Example 7, starting from 2.83 g of 1-(2-chloro phenyl) isoquinoline 3-carboxylic acid, 1.15 g of triethylamine, 1.24 g of ethyl chloroformate and 1.56 g of N-methyl benzylamine in 100 ml of chloroform. 2.5 g of N-methyl N-phenylmethyl 1-(2-chloro phenyl) isoquinoline 3-carboxamide, melting at 128° C., are obtained.

EXAMPLE 18

N-cyclohexyl N-methyl 1-(2-chloro phenyl) isoquinoline 3-carboxamide

Operations are carried out as for Example 7, starting from 2.83 g of 1-(2-chloro phenyl) isoquinoline 3-carboxylic acid, 1.15 g of triethylamine, 1.24 g of ethyl chloroformate and 1.46 g of N-methyl cyclohexylamine in 100 ml of chloroform. 2.45 g of N-cyclohexyl N-methyl 1-(2-chloro phenyl) isoquinoline 3-carboxamide melting at 131° C., are obtained.

EXAMPLE 19

N-methyl N-(1-methyl propyl) 1-(2-chloro phenyl) 7-methyl isoquinoline 3-carboxamide 3 g of 1-(2-chloro phenyl) 7-methyl isoquinoline 3-carboxylic acid in 30 ml of thionyl chloride are brought to boiling point. After reaction, the thionyl chloride is evaporated, and the residue taken up in 30 ml of toluene, which is again evaporated. The residue is redissolved in 30 ml of toluene, and a solution of 2.61 g of N-methyl 2-butanamine in 10 ml of toluene, is added. After 4 h, the toluene is evaporated, the residue is taken up in methylene chloride, the organic phase washed with an aqueous solution of sodium carbonate, dried over magnesium sulphate and evaporated to dryness under reduced pressure. The residue is chromatographed on silica gel using a cyclohexane-ethyl acetate (1:1), mixture as eluant. After recrystallization from ether, 1.95 g of N-methyl N(1-methyl propyl) 1-(2-chloro phenyl) 7-methyl isoquinoline 3-carboxamide, melting at 132° C., is obtained.

1-(2-chloro phenyl) 7-methyl isoquinoline 3-carboxylic acid is obtained by the action of aluminum chloride (0.219 mole) on 2-(2-chloro phenyl) 4-[(4-methyl phenyl) methylene] 4H 5-oxazolone (0.073 mole) in 160 ml of tetrachloroethane, at ambient temperature. It has a melting point of 160° C.

EXAMPLE 20

N,N-diethyl 1-(2-chloro phenyl) 7-methyl isoquinoline 3-carboxamide

Operations are carried out as for Example 19, starting from 3 g of 1-(2-chloro phenyl) 7-methyl isoquinoline 3-carboxylic acid, 30 ml of thionyl chloride, 1.46 g of diethylamine and 40 ml of toluene.

2.08 g of N,N-diethyl 1-(2-chloro phenyl) 7-methyl isoquinoline 3-carboxamide, melting at 162° C. are obtained.

EXAMPLE 21

N-methyl N-(1-methyl propyl) 1-(2-chloro phenyl) isoquinoline 3-carboxamide

Operations are carried out as for Example 7, starting from 1.68 g of 1-(2-chloro phenyl) isoquinoline 3-carboxylic acid, 0.7 g of triethylamine, 0.75 g of ethyl chloroformate and 0.68 g of N-methyl 2-butanamine in 60 ml of chloroform. 1.4 g of N-methyl N(1-methyl propyl) 1-(2-chloro phenyl) isoquinoline 3-carboxamide, melting at 136° C., is obtained.

EXAMPLE 22

N,N-diethyl 7-chloro 1-(2-chloro phenyl) isoquinoline 3-carboxamide

Operations are carried out as for Example 7, starting from 3.18 g of 7-chloro 1-(2-chloro phenyl) isoquinoline 3-carboxylic acid, 1.16 g of triethylamine, 1.25 g of ethyl chloroformate and 0.95 g of diethylamine in 100 ml of chloroform. 2.2 g of N,N-diethyl 7-chloro 1-(2-chloro phenyl) isoquinoline 3-carboxamide, melting at 145° C., are obtained.

7-chloro 1-(2-chloro phenyl) isoquinoline 3-carboxylic acid is obtained by the action of aluminum chloride (0.33 mole) on 2-(2-chloro phenyl) 4-[(4-chloro phenyl) methylene] 4H 5-oxazolone (0.11 mole) in 460 ml of tetrachloroethane, at 60° C. It has a melting point of 180°–182° C.

EXAMPLE 23

1-[3-[1-(2-chloro phenyl) isoquinolyl]carbonyl] 4-methyl piperazine

Operations are carried out as for Example 7, starting from 2.13 g of 1-(2-chloro phenyl) isoquinoline 3-carboxylic acid, 0.88 g of triethylamine, 0.95 g of ethyl chloroformate and 0.95 g of N-methyl piperazine, in 75 ml of chloroform. 1.05 g of 1-[3-[1-(2-chloro phenyl) isoquinolyl]carbonyl] 4-methyl piperazine, melting at 139° C., is obtained.

EXAMPLE 24

N,N-di(1-methyl ethyl) 1-(2-chloro phenyl) isoquinoline 3-carboxamide

Operations are carried out as for Example 7, starting from 2.83 g of 1-(2-chloro phenyl) isoquinoline 3-carboxylic acid, 1.17 g of triethylamine, 1.25 g of ethyl chloroformate and 1.31 g of di-isopropylamine in 100 ml of chlorofom. 0.85 g of N,N-di(1-methyl ethyl) 1-(2-chloro phenyl) isoquinoline 3-carboxamide, melting at 161° C., is obtained.

EXAMPLE 25

N-methyl N(1-methyl propene-2-yl) 1-(2-chloro phenyl) isoquinoline 3-carboxamide Operations are carried out as for Example 7, starting from 9.2 g of 1-(2-chloro phenyl) isoquinoline 3-carboxylic acid, 3.8 g of triethylamine, 4.08 g of ethyl chloroformate and 3.6 g of N-methyl 1-methyl-propene-2-yl amine in 325 ml of chloroform. 7.9 g of N-methyl N(1-methyl propene-2-yl) 1-(2-chloro phenyl) isoquinoline 3-carboxamide, melting at 108° C., are obtained.

EXAMPLE 26

N-methyl N-(1-methyl propyl) 1-(2-thienyl) isoquinoline 3-carboxamide

Operations are carried out as for Example 7, starting from 3 g of 1-(2-thienyl) isoquinoline 3-carboxylic acid, 1.73 g of triethylamine, 1.86 g of ethyl chloroformate and 1.69 g of N-methyl 2-butanamine in 150 ml of chloroform. 2.5 g of N-methyl N-(1-methyl propyl) 1-(2-thienyl) isoquinoline 3-carboxamide, melting at 146° C. are obtained.

1-(2-thienyl) isoquinoline 3-carboxylic acid is obtained by the action of aluminum chloride (0.42 mole) on 4-phenyl methylene 2-(2-thienyl) 4H 5-oxazolone (0.14 mole) in 300 ml of tetrachloroethane. It has a melting point of 162° C.

EXAMPLE 27

N,N-diethyl 1-(4-chloro phenyl) isoquinoline 3-carboxamide

Operations are carried out as for Example 7, starting from 2.83 g of 1-(4-chloro phenyl) isoquinoline 3-carboxylic acid, 1.15 g of triethylamine, 1.24 g of ethyl chloroformate and 0.95 of diethylamine in 100 ml of chloroform. 1.55 g of N,N-diethyl 1-(4-chloro phenyl) isoquinoline 3-carboxamide, melting at 122° C., is obtained.

1-(4-chloro phenyl) isoquinoline 3-carboxylic acid is obtained from 1-(4-chloro phenyl) 3-methyl isoquinoline. By means of N-bromosuccinimide, 1-(4-chloro phenyl) 3-dibromomethyl isoquinoline is first formed, which is then oxidized with silver nitrate, initially in a neutral medium, and then in a basic medium. This acid has a melting point of 232°–234° C.

EXAMPLE 28

N,N-dimethyl 6,7-dimethoxy 1-phenyl isoquinoline 3-carboxamide

Operations are carried out as for Example 4, starting from 1.26 g of ethyl 6,7-dimethoxy-1-phenyl isoquinoline 3-carboxylate, 0.81 g of diethylamine and 4.6 g of 1.6M butyl lithium in hexane, in 50 ml of tetrahydrofuran. 0.95 g of N,N-diethyl 6,7-dimethoxy 1-phenyl isoquinoline 3-carboxamide melting at 134° C., is obtained.

Ethyl 6,7-dimethoxy 1-phenyl isoquinoline 3-carboxylate may be prepared according to T. HOSONO, J. Pharm Soc. Japan, 65, No. 7/8a, 11 (1945).

EXAMPLE 29

N-methyl N-(1-methyl propyl) 7-phenyl thieno[2,3-c]pyridine 5-carboxamide

Operations are carried out as for Example 7, starting from 3.82 g of 7-phenyl thieno[2,3-c]pyridine 5-carboxylic acid, 1.74 g of triethylamine, 1.87 g of ethyl chloroformate and 1.7 g of N-methyl 2-butanamine in 150 ml of chloroform. 3.15 g of N-methyl N-(1-methyl propyl) 7-phenyl thieno[2,3-c]pyridine 5-carboxamide, melting at 117° C., are obtained.

7-phenyl thieno[2,3-c]pyridine 5-carboxylic acid is obtained by the action of aluminum chloride (0.225 mole) on 2-phenyl-4-[(3-thienyl methylene] 4H 5-oxazolone (0.075 mole) in 150 ml of tetrachloroethane, at ambient temperature. It has a melting point of 208° C.

EXAMPLE 30

N-methyl N-(1-methyl propyl) 4-phenyl thieno[3,2-c]pyridine 6-carboxamide

Operations are carried out as for Example 7, starting from 3.82 g of 4-phenyl thieno[3,2-c]pyridine 6-carboxylic acid, 1.74 g of triethylamine, 1.87 g of ethyl chloroformate and 1.7 g of N-methyl 2-butanamine in 150 ml of chloroform. 1.9 g of N-methyl N-(1-methyl propyl) 4-phenyl thieno[3,2-c]pyridine 6-carboxamide, melting at 104° C. is obtained.

4-phenyl thieno[3,2-c]pyridine 6-carboxylic acid is obtained by the action of aluminum chloride (0.352 mole) on 2-phenyl 4-[2-thienyl methylene] 4H 5-oxazolone (0.117 mole) in 235 ml of tetrachloroethane, at ambient temperature. It has a melting point of 165° C.

EXAMPLE 31

N,N-diethyl 4-(2-chloro phenyl) thieno[3,2-c]pyridine 6-carboxamide

Operations are carried out as for example 7, starting from 2.9 g of 4-(2-chloro phenyl) thieno[3,2-c]pyridine 6-carboxylic acid, 1.17 g of triethylamine, 1.25 g of ethyl chloroformate and 0.94 g of diethylamine in 100 ml of chloroform. 2.1 g of N,N-diethyl 4-(2-chloro phenyl) thieno[3,2-c]pyridine 6-carboxamide, melting at 119° C., are obtained.

4-(2-chloro phenyl) thieno[3,2-c]pyridine 6-carboxylic acid is obtained by the action of aluminum chloride (0.103 mole) on 2-(2-chloro phenyl) 4-[2-thienyl methylene] 4H 5-oxazolone (0.034 mole) in 145 ml of 1,1,2,2-tetrachloro ethane, at 60° C. It has a melting point of 210° C.

EXAMPLE 32

N,N-diethyl 7-(2-chloro phenyl) thieno[2,3-c]pyridine 5-carboxamide

Operations are carried out as for Example 7, starting from 2.9 g of 7-(2-chloro phenyl) thieno[2,3-c]pyridine 5-carboxylic acid, 1.17 g of triethylamine, 1.25 g of ethyl chloroformate and 0.94 g of diethylamine in 100 ml of chloroform. 1.4 g of N,N-diethyl 7-(2-chloro phenyl) thieno[2,3-c]pyridine 5-carboxamide, melting at 86° C., is obtained.

7-(2-chloro phenyl) thieno[2,3-c]pyridine 5-carboxylic acid is obtained by the action of aluminum chloride (0.342 mole) on 2-(2-chloro phenyl) 4-[3-thienyl methylene] 4H 5-oxazolone (0.114 mole) in 475 ml of 1,1,2,2-tetrachloroethane, at 60° C. It has a melting point of 152° C.

EXAMPLE 33

N,N-diethyl 4-phenyl quinazoline 2-carboxamide

Operations are carried out as for Example 19, starting from 2.5 g of 4-phenyl quinazoline 2-carboxylic acid, 10 ml of thionyl chloride 25 ml of toluene and 25 ml of diethylamine. 1.27 g of N,N-diethyl 4-phenyl quinazoline 2-carboxamide, melting at 101° C., is obtained.

4-phenyl quinazoline 2-carboxylic acid is obtained by the action of methyl oxalyl chloride on 2-amino-benzophenone in pyridine. The N-(methyloxalyl) 2-benzoyl aniline thus formed being then treated with ammonium acetate in acetic acid, at boiling point. The acid has a melting point of 167° C.

EXAMPLE 34

N-methyl N-(1-methyl propyl) 4-phenyl quinazoline 2-carboxamide

Operations are carried out as for Example 19, starting from 2.5 g of 4-phenyl quinazoline 2-carboxylic acid, 10 ml of thionyl chloride, 25 ml of toluene and 10 ml of N-methyl 2-butanamine. 2.2 g of N-methyl N-(1-methyl propyl) 4-phenyl quinazoline 2-carboxamide, melting at 128° C., are obtained.

EXAMPLE 35

N-methyl N(1-methyl propyl) 4-(2-fluorophenyl) quinoline 2-carboxamide 3.3 g of 4-(2-fluorophenyl) quinoline 2-carboxylic acid in 10 ml of thionyl chloride are brought to boiling point. After reaction, the thionyl chloride is evaporated and the residue taken up in 30 ml of toluene which is again evaporated. The residue is redissolved in 100 ml of toluene and 4.8 ml of triethylamine, then under agitation, 1.8 g of N-methyl 2-butanamine hydrochloride are added. After 14 h. the reaction mixture is taken up in 100 ml of water. The organic phase is decanted, the aqueous phase is extracted 3 times each with 100 ml of ether. The organic phases are washed with water, dried over magnesium sulphate and evaporated under reduced pressure. The residue is chromatographed on silica gel using a cyclohexane/ethylacetate (70:30) mixture as eluant. After recrystallization in isopropylether/ether (5:2) mixture, 1.16 g of N-methyl N-(1-methylpropyl) 4-(2-fluorophenyl) quinoline 2-carboxamide melting at 86° C. is obtained.

4-(2-fluorophenyl) quinoline 2-carboxylic acid is obtained by the action of concentrated HCl (400 ml) on 2-tribromomethyl 4-(2-fluorophenyl) quinoline 48 h at reflux temperature. It has a melting point of 210° C.

2-tribromomethyl 4-(2-fluorophenyl) quinoline is obtained by the action of bromine (2.7 $10^{-1}$ mole) in solution in acetic acid (36 ml) on 4-(2-fluorophenyl) 2-methyl quinoline (4.6 $10^{-2}$ mole) in solution in acetic acid (55 ml) in the presence of sodium acetate (1.8 $10^{-1}$ mole) and acetic anhydride (4.9 $10^{-2}$ mole).

4-(2-fluorophenyl) 2-methyl quinoline is obtained by the action of acetone (5.6 $10^{-2}$ mole) on (2-amino phenyl) (2-fluorophenyl) methanone (5.6 $10^{-2}$ mole) in acetic acid (60 ml) in the presence of sulfuric acid (0.6 ml). It has a melting point of 119° C.

EXAMPLE 36

N-methyl N-(1-methyl propyl) 4-(4-methoxy phenyl) quinoline 2-carboxamide

Operations are carried out as for Example 35, starting from 2.1 g of 4-(4-methoxy phenyl) quinoline 2-carboxylic acid, 6.4 ml of thionyl chloride and 1.4 g of N-methyl 2-butanamine.

After chromatography on silica gel using a cyclohexane-ethylacetate (60:40) mixture as eluant and recrystallization from isopropyl ether, 0.77 g of N-methyl N-(1-methyl propyl)4-(4-methoxy phenyl) quinoline 2-carboxamide, melting at 114° C. is obtained.

4-(4-methoxy phenyl) quinoline 2-carboxylic acid is obtained by double oxidation of the 4-(4-methoxy phenyl) 2-methyl quinoline (5.6 $10^2$ mole) in 4-(4-methoxy phenyl) quinoline 2-carboxaldehyde with selenium dioxide (5.6 $10^{-2}$ mole) in 50 ml of a dioxane-water (9:1) mixture, then in 4-(4-methoxy phenyl) quinoline 2-carboxylic acid by action, on the aldehyde (2.2 $10^{-2}$ mole) of H$_2$O$_2$ 110 vol. (18 ml) in acetone (200 ml). 4-(4-methoxy phenyl) quinoline 2-carboxylic acid melts at 213° C. (A first melting is observed at 130° C. with resolidification.)

4-(4-methoxy phenyl) 2-methyl quinoline is prepared by the action of acetone (1.48 $10^{-1}$ mole) on (2-amino phenyl) (4-methoxy phenyl) methanone (7.4 $10^{-2}$ mole) in acetic acid (85 ml) in the presence of sulfuric acid (0.85 ml). It has a melting point of 101° C.

(2-amino phenyl) (4-methoxy phenyl) methanone is prepared according to Ullmann and Bleier, Ber, 35, 4278 (1902).

EXAMPLE 37

N,N-diethyl 4-(4-methoxy phenyl) quinoline 2-carboxamide

Operations are carried out as for Example 1, starting from 21 g of 4-(4-methoxy phenyl) quinoline 2-carboxylic acid, 64 ml of thionyl chloride and 39 ml of diethylamine. 2.2 g of N,N-diethyl 4-(4-methoxy phenyl) quinoline 2-carboxamide are obtained. After recrystallization in isopropyl ether the product melts at 91° C.

EXAMPLE 38

N,N-diethyl 4-(3-nitro phenyl) quinoline 2-carboxamide

Operations are carried out as for Example 1, starting from 57 g of 4-(3-nitro phenyl) quinoline 2-carboxylic acid, 28.5 ml of thionyl chloride and 9.9 ml of diethylamine in 50 ml of toluene.

After chromatography on silica gel using a chloroformether (90:10) mixture as eluant then a second chromatography using a cyclohexane-diethyl amine (90:10) mixture is carried out. 1 g of N,N-diethyl 4-(3-nitro phenyl) quinoline 2-carboxamide is obtained in the form of a brown laquer.

| N.M.R. spectrum of the product obtained aromatic protons: | $\delta$ = 7.3 to 8.4 p.p.m. |
|---|---|
| 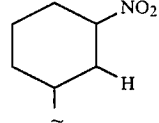 | $\delta$ = 8.4 p.p.m. |
| 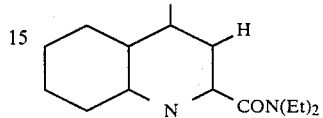 | $\delta$ = 7.6 p.p.m. |

4-(3-nitro phenyl) quinoline 2-carboxylic acid is prepared by analogy as 4-(4-methoxy phenyl) quinoline 2-carboxylic acid described in Example 36 starting from 2-methyl 4-(3-nitro phenyl) quinoline (2.46 $10^{-2}$ mole), 2.73 g of selenium dioxide and 20.9 ml H$_2$O$_2$ 110 vol.

2-methyl 4-(3-nitro phenyl) quinoline is prepared by nitration at 0° C. of 2-methyl 4-phenyl quinoline (1.36 $10^{-1}$ mole) with sulfonitric mixture (90 ml nitric acid 60% and 90 ml concentrated sulfuric acid) and separation of isomers. It has a melting point of 157° C.

2-methyl 4-phenyl quinoline is prepared according to Geigy and Koenigs, Ber, 18, 2406 (1885).

EXAMPLE 39

N,N-dibutyl 1-phenyl isoquinoline 3-carboxamide

Operations are carried out as for Example 7, starting from 2.5 g of 1-phenyl isoquinoline 3-carboxylic acid, 1.15 g of triethylamine, 1.24 g of ethyl chloroformate and 1.66 g of dibutylamine in 100 ml of toluene. After chromatography and recrystallization in petroleum ether, 1.5 g of N,N-dibutyl 1-phenyl isoquinoline 3-carboxamide melting at 62° C. is obtained.

EXAMPLE 40

2-ethyl 1-[(1-phenyl 3-isoquinolyl) carbonyl]piperidine

Operations are carried out as for Example 7, starting from 2.5 g of 1-phenyl isoquinoline 3-carboxylic acid, 1.15 g of triethylamine, 1.24 g of ethyl chloroformate and 1.46 g of 2-ethyl piperidine in 100 ml of toluene.

After recrystallization in petroleum ether, 2.2 g of 2-ethyl 1-[(1-phenyl 3-isoquinolyl) carbonyl]piperidine melting at 86° C. is obtained.

EXAMPLE 41

2(R)-ethyl 1-[(1-phenyl 3-isoquinolyl) carbonyl]piperidine

Operations are carried out as for Example 7, starting from 2.5 g of 1-phenyl isoquinoline 3-carboxylic acid, 2.86 g of triethylamine, 1.24 g of ethyl chloroformate and 1.93 g of 2(R)-ethyl piperidine hydrochloride in 100 ml of toluene. After chromatography, 2 g of 2(R)-ethyl 1-[(1-phenyl 3-isoquinolyl) carbonyl]piperidine in the form of oil are obtained. $\alpha_D^{26}$ = +1.4° (2% in ethanol).

EXAMPLE 42

2(S)-ethyl 1-[(1-phenyl 3-isoquinolyl) carbonyl]piperidine

Operations are carried out as for Example 7, starting from 2.5 g of 1-phenyl isoquinoline 3-carboxylic acid, 1.15 g of triethylamine, 1.24 g of ethyl chloroformate and 1.2 g of 2(S)-ethyl piperidine in 100 ml of toluene. After chromatography, 3 g of 2(S)-ethyl 1-[(1-phenyl 3-isoquinolyl) carbonyl]piperidine in the form of oil are obtained. $\alpha_D^{23} = -2.4°$ (2% in ethanol).

EXAMPLE 43

N,N-diethyl 1-(3-trifluoromethyl phenyl) isoquinoline 3-carboxamide

Operations are carried out as for Example 7, starting from 1.55 g of 1-(3-trifluoromethyl phenyl) isoquinolyl 3-carboxylic acid, 0.57 g of triethylamine, 0.62 g of ethyl chloroformate and 0.48 g of diethylamine in 50 ml of toluene. After recrystallization in petroleum ether, 0.95 g of N,N-diethyl 1-(3-trifluoromethyl phenyl) isoquinoline 3-carboxamide melting at 76° C. is obtained.

1-(3-trifluoromethyl phenyl) isoquinoline 3-carboxylic acid is obtained from 3-methyl 1-(3-trifluoromethyl phenyl) isoquinoline. By means of N-bromo succinimide, the 3-dibromomethyl 1-(3-trifluoromethyl phenyl) isoquinoline is obtained and treated with silver nitrate in neutral media then alkaline media. It has a melting point of 170° C.

EXAMPLE 44

N-methyl N-1-(S)-methyl propyl) 1-(2-chloro phenyl) isoquinoline 3-carboxamide

Operations are carried out as for Example 7, starting from 1.7 g of 1-(2-chloro phenyl) isoquinoline 3-carboxylic acid, 2.1 g of triethylamine, 0.75 g of ethyl chloroformate and 0.96 g of N-methyl 2(S)-butanamine, HCl in 60 ml of toluene. After chromatography and recrystallization in cyclohexane, 0.5 g of N-methyl N-(1-(S)-methyl propyl) 1-(2-chlorophenyl) isoquinoline 3-carboxamide melting at 134° C. is obtained. $\alpha_D^{27} = +53.7°$ (0.5% in CHCl$_3$).

EXAMPLE 45

N-methyl N-(1(R)methyl propyl) 1-(2-chloro phenyl) isoquinoline 3-carboxamide

Operations are carried out as for Example 7, starting from 1.7 of 1-(2-chloro phenyl) isoquinoline 3-carboxylic acid, 0.75 g of ethyl chloroformate, 2.1 g of triethylamine and 0.96 g of N-methyl 2-(R)butanamine hydrochloride in 60 ml of toluene. After chromatography and recrystallization in cyclohexane, 0.6 g of N-methyl N-(1-(R)methyl propyl) 1-(2-chloro phenyl) isoquinoline 3-carboxamide melting at 134° C. is obtained. $\alpha_D^{27} = -51°$ (0.5% in CHCl$_3$).

EXAMPLE 46

N-methyl N-(1-methyl propyl) 7-(2-chloro phenyl) thieno[2,3-c]pyridine 5-carboxamide Operations are carried out as for Example 7, starting from 3.5 g of 7-(2-chloro phenyl) thieno[2,3-c]pyridine 5-carboxylic acid, 5.85 ml of triethylamine, 1.33 ml of ethyl chloroformate and 1.94 g of N-methyl 2-butanamine hydrochloride in 60 ml of CHCl$_3$. After recrystallization in petroleum ether, 0.6 g of N-methyl N-(1-methyl propyl) 7-(2-chloro phenyl) thieno[2,3-c]pyridine 5-carboxamide melting at 97° C. is obtained.

EXAMPLE 47

N-methyl N-(1-methyl propyl) 4-(2-chloro phenyl) thieno[3,2-c]pyridine 6-carboxamide Operations are carried out as for Example 7, starting from 10 g of 4-(2-chloro phenyl) thieno[3,2-c]pyridine 6-carboxylic acid, 11.9 ml of triethylamine, 4 ml of ethyl chloroformate and 4.8 ml of N-methyl 2-butanamine in 200 ml of CHCl$_3$. After chromatography and recrystallization in petroleum ether, 1 g of N-methyl N-(1-methyl propyl) 4-(2-chloro phenyl) thieno[3,2-c]pyridine 6-carboxamide melting at 82° C. is obtained.

PHARMACOLOGICAL PROPERTIES

Affinity for "peripheral" receptor sites of benzodiazepines

This affinity is measured by the capacity of the products to displace tritiated diazepam ($^3$H-diazepam) from its binding site, and is expressed by a value Ki, in nanomoles (nM), which is calculated by the formula:

$$Ki = \frac{IC_{50}}{1 + \frac{C}{KD}}$$

in which C represents the concentration of $^3$H-diazepam used (1 mM), $K_D$ is an affinity constant equal to 15 nM, and IC$_{50}$ is the concentration necessary to obtain inhibition of 50% of the binding of $^3$H diazepam.

The products have been studied according to the method of C. BRAESTRUP et al, Proc. Natl. Acad. Sci. USA, 1977, 74, 3805, on kidney membranes from the rat.

As an example, the following results have been obtained:

| Products | Ki (nM) | Products | (Ki (nM)) |
| --- | --- | --- | --- |
| Example 1 | 5.4 | Example 16 | 0.9 |
| Example 3 | 27 | Example 17 | 117 |
| Example 5 | 150 | Example 21 | 8 |
| Example 6 | 17 | Example 24 | 20 |
| Example 7 | 210 | Example 25 | 3 |
| Example 10 | 2 | Example 31 | 9 |
| Example 11 | 9 | Example 32 | 6.3 |
| Example 12 | 99 | Example 33 | 27 |
| Example 13 | 72 | Example 35 | 2 |
| Example 14 | 18 | Example 38 | 30 |
| Example 15 | 20 | Example 39 | 21 |
| Example 46 | 7 | Example 40 | 16 |
| Example 47 | 1 | Example 41 | 22 |
|  |  | Example 42 | 13 |
|  |  | Example 43 | 13 |
|  |  | Example 44 | 19 |
|  |  | Example 45 | 9 |

TOXICOLOGICAL PROPERTIES

The acute toxicities of the compounds according to the invention, have been determined on the male mouse CD1 (Charles RIVER) by the oral route. LD$_{50}$ values have been calculated after 3 days of observation, by the cumulative method of J. J. REED and H. MUENCH (Amer. J. Hyg. 1938, 27, 493).

The compounds behaved as relatively non-toxic substances in the mouse, since the LD$_{50}$ values of the compounds were between 200 and 1000 mg/kg.

THERAPEUTIC USE

The compounds of the invention can be used in human therapy, in the form of tablets, capsules, gelatin-coated tablets, suppositories, ingestible or injectable solutions, for the treatment of pulmonary, renal, cardiovasculatory and circulatory disorders, for the treatment of pathological states associated with immunological disorders, for the treatment of states of aggressivity and in the various indications for benzodiazepines (for example as anticonvulsivants and anxiolytics).

The pharmaceutical compositions of this invention will contain the active compound together with a solid or liquid pharmaceutically acceptable nontoxic carrier. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerols solutions are also be employed as liquid carriers, particularly for injectable solutions. Suitable pharmaceutical excipients include starch, glucose, lactose, sucrose, gelatine, malt, rice, flour, chalk, silica gel, magnesium carbonate, magnesium stearate, sodium stearate, glycerol monostearate, talc, sodium chloride, dried skim milk, glycerol, propylene glycol, water, ethanol and the like. These compositions can take the form of solutions, suspensions, tablets, pills, capsules, powders, sustained release formulations and the like. Suitable pharmaceutical carriers are described in "Remington's Pharmaceutical Sciences" by E. W. Martin. Such compositions will contain an effective therapeutic amount of the active compound together with a suitable amount of carrier so as to provide the form for proper administration to the host. While intravenous injection is a very effective form of administration, other modes can be employed.

The posology depends on the effects required and the method of administration used. For example, by the oral route, it may be between 20 and 100 mg of active substance per day, with unit doses of from 5 to 200 mg.

Another feature of the invention resides in the pharmacologically active compositions having an affinity for the receptor sites of $^3$H-diazepam which contain as the active ingredient an effective amount of a component of the formulae I, II, III and IV together with a carrier as set forth.

Another feature of the invention resides in medicaments usable for treatment or circulating, renal, cardiovascular or circulatory disorders, for treatment of pathological states associated with immunological disorders for the treatment of states of aggression and in the applications of benzodiazepines, containing an effective amount of a compound of formulae I, II, III and IV.

A still further feature resides in treating warm blooded mammals for the above mentioned disorders and states by administering, as mentioned above, an effective amount of a compound of the formula I, II, III and IV.

We claim:
1. A compound of the formula:

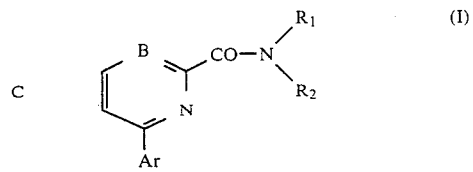

in which $R_1$ and $R_2$ independently represent a linear or branched alkyl containing 1 to 6 carbon atoms, cycloalkyl containing 3 to 7 carbon atoms, phenyl alkyl or cycloalkyl alkyl, the alkyl part of which contains 1 to 3 carbon atoms, $R_1$ and $R_2$ further represent alkenyl or alkynyl containing 3 to 6 carbon atoms, with the proviso that the double or triple bond is not situated in position 1-2 in relation to the nitrogen atom, $R_1$ and $R_2$ may further represent a group of the formula —$R_3$—Z—$R_4$, in which $R_3$ represents linear or branched alkylene with 2 to 6 carbon atoms, with the proviso that at least 2 carbon atoms separate the nitrogen atom from group Z;

$R_4$ represents alkyl having from 1 to 4 carbon atoms and Z is oxygen or sulphur or >N—$R_5$, $R_5$ represents hydrogen or alkyl with 1 to 3 carbon atoms, Ar represents phenyl, pyridyl or thienyl, or phenyl substituted with one or two substituents selected from halogen atoms, alkyl, alkoxy and alkylthio with 1 to 4 carbon atoms, trifluoromethyl and nitro, A and B represent independently, N or CH—, C represents the linkage

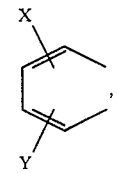

or when A represents N and B represents CH, one of the following linkages:

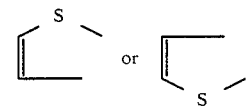

X, Y represent independently, hydrogen, halogen, alkyl or alkoxy containing 1 to 3 carbon atoms, nitro or trifluoromethyl, and

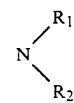

represents a heterocyclic ring which is pyrrolidine, piperidine, morpholine or piperazine ring which may be substituted on the nitrogen by alkyl containing 1 to 3 carbon atoms.

2. A compound according to claim 1, of the formula:

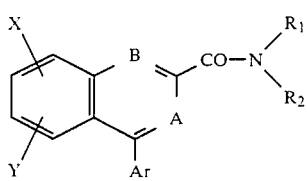

in which A, B, Ar, $R_1$, $R_2$, X and Y have the same meaning as in claim 1.

3. A compound according to claim 1, of the formula:

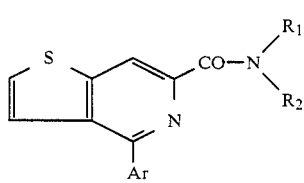

in which Ar, $R_1$, $R_2$ have the same meaning as in claim 1.

4. A compound according to claim 1, of the formula:

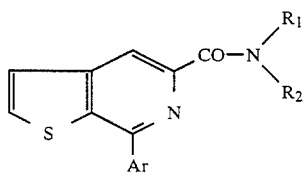 (IV)

in which Ar, $R_1$ and $R_2$ have the same meaning as in claim 1.

5. A compound according to claim 1, of the formula:

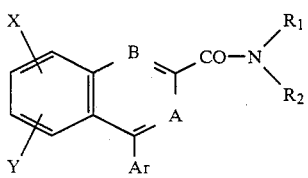 (II)

in which A, B, Ar, X and Y have the same meaning as in claim 1 and

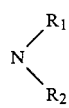

represents a pyrrolidine, piperidine, morpholine, or piperazine ring, which may be substituted on the nitrogen by alkyl containing 1 to 3 carbon atoms.

6. A compound according to claim 1, of the formula:

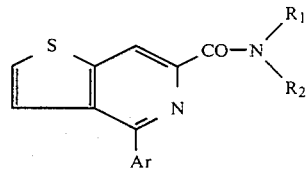

in which Ar has the same meaning in claim 1 and

represents a pyrrolidine, piperidine, morpholine, or piperazine ring, which may be substituted on the nitrogen by alkyl containing 1 to 3 carbon atoms.

7. A compound according to claim 1, of the formula:

 (IV)

in which Ar has the same meaning in claim 1 and represents a pyrrolidine, piperidine, morpholine, or piperazine ring, which may be substituted on the nitrogen by alkyl containing 1 to 3 carbon atoms.

8. A compound according to claims 1, 2, 3, 4, 5, 6 or 7 in which the group contains an asymmetric carbon atoms and which is an enantiomorphic or racemic compound.

9. A pharmacologically active composition having an affinity for the receptor sites of $^3$H-diazepam, comprising as the active ingredient an effective amount of a compound according to claim 1 and a solid or a liquid pharmaceutically acceptable nontoxic carrier.

10. A medicament usable in particular for the treatment of pulmonary, renal, cardiovascular or circulatory disorders, for the treatment of pathological states associated with immunological disorders, for the treatment of states of aggresivity and in the applications of benzodiazepines, comprising an effective amount of a compound according to claims 1, 2, 3 or 4 and a solid or a liquid pharmaceutically acceptable nontoxic carrier.

11. A method of treating a warm blooded mammal for a pulmonary, renal, cardiovascular or circulatory disorder, for pathological states associated with immunological disorders, for states of aggressivity and in the application of benzodiazepines comprising administering an effective amount of the compound of claim 1.

* * * * *